United States Patent [19]

Preugschas et al.

[11] 4,021,226
[45] May 3, 1977

[54] HERBICIDES

[75] Inventors: Helmut Preugschas; Ewald Daubach, both of Ludwigshafen; Roman Fischer, Mutterstadt; Manfred Herrmann, Ludwigshafen, all of Germany

[73] Assignee: BASF Aktiengesellschaft, Ludwigshafen (Rhine), Germany

[22] Filed: Oct. 8, 1975

[21] Appl. No.: 620,712

[30] Foreign Application Priority Data

Nov. 9, 1974 Germany .................. 2453255

[52] U.S. Cl. .................. 71/92; 71/DIG. 1
[51] Int. Cl.$^2$ .................. A01N 9/22
[58] Field of Search .................. 71/92, DIG. 1

[56] References Cited

UNITED STATES PATENTS 3,210,353  10/1965  Reicheneder et al. .......... 71/92

FOREIGN PATENTS OR APPLICATIONS 1,113,457  5/1959  Germany .................. 71/92
1,178,081  9/1964  Germany .................. 71/92

*Primary Examiner*—Lewis Gotts
*Assistant Examiner*—Catherine L. Mills
*Attorney, Agent, or Firm*—Johnston, Keil, Thompson & Shurtleff

[57] ABSTRACT

New and valuable herbicide based on 1-phenyl-4-amino-5-chloro (or -5-bromo)-pyridazone-(6) in the form of an aqueous suspension.

7 Claims, No Drawings

HERBICIDES

The present invention relates to a herbicide based on 1-phenyl-4-amino-5-chloro (or -5-bromo)-pyridazone-(6) in the form of an aqueous suspension.

It is known to use pyridazones, especially 1-phenyl-4-amino-5-chloropyridazone-(6), for controlling the growth of unwanted plants. The active ingredient is usually employed in the form of a liquor which is sprayed on to the plants and which is prepared from dry fine powder by suspending it in water. The disadvantage of this form of application is that the herbicidal action, particularly in a dry climate, is slow to set in and is often unsatisfactory. This is in part attributable to the poor quality of the liquor; irregular and sometimes coarse powder particles; non-uniform distribution of the herbicide on plants and soil; and lack of penetration by the active ingredient of the leaf surface of unwanted plants, which undergo change in periods of continued dryness. These disadvantages are particularly evident in the fight against such important weeds as *Alopecurus spp.*, *Anagallis arvensis*, *Anthemis spp.*, *Amaranthus spp.* *Avena spp.*, *Capsella bursa pastoris*, *Centaurea cyanus*, *Chenopodium spp.*, *Digitaria sanguinalis*, *Echinochloa crus-galli*, *Euphorbia spp.*, *Fumaria spp.*, *Galeopsis spp.*, *Galium aparine*, *Galinsoga parviflora*, *Lamium spp.*, *Matricaria spp.*, *Mercurialis annua*, *Polygonum spp.*, *Raphanus raphanistrum*, *Senecio vulgaris*, *Setaria spp.*, *Sinapis arvensis*, *Sohchus spp.*, *Stellaria media*, *Thlaspi arvense*, *Veronica spp.*, and *Vicia spp.*

We have now found that these drawbacks do not occur when a herbicide based on 1-phenyl-4-amino-5-chloropyridazone-(6) or 1-phenyl-4-amino-5-bromopyridazone-(6) is used which contains from 10 to 65 wt% of the active ingredient in the form of an aqueous suspension and, as dispersant, a condensation product of sulfonated phenols free from condensed ring systems with urea and formaldehyde, which condensation product has been aftertreated with phenols and formaldehyde. The aqueous suspension is highly concentrated and is diluted with water before use to the desired concentration. In addition to their good action, the herbicides of the invention offer the following additional advantages. The dispersions are extremely stable, even after prolonged storage periods. They can be readily mixed with other plant protection agents upon dilution. No dust problems occur when the spray liquors are prepared for use.

The condensation products are prepared in a two-stage reaction from sulfonated phenols which are free from condensed ring systems, urea and formaldehyde (in a molar ratio of 1:1 to 1.5:1.7 to 2.2); the condensates obtained are after-treated with phenols and formaldehyde. This after treatment may be effected either by reaction with phenols and formaldehyde or by separate preparation of a reaction product of phenols and formaldehyde and subsequent condensation of this product with the abovementioned condensate (German Pat. No. 1,113,457 and 1,178,081).

It is surprising that these condensation products impart to the suspensions of the invention such a considerably increased stability compared with other dispersing agents.

To improve the herbicidal action still futher, spreader stickers, water-emulsifiable oils and other herbicidal agents may be added to the herbicides themselves or to the aqueous spray liquors prepared from them.

The aqueous suspension according to the invention may be diluted with water in any desired ratio; the concentration of the active ingredient in the spray liquor may for instance be from 0.1 to 10 wt.%.

In a prior art spray powder, the particle size distribution of the active ingredient is for instance as follows:
20 wt% smaller than 5 $\mu$;
40 wt% smaller than 10 $\mu$;
70 wt% smaller than 20 $\mu$.

In the suspension according to the invention, at least 80 wt% of the active ingredient particles are smaller than 2 $\mu$.

The application rate of the active ingredients for one-shot use is for example from 0.1 to 15, preferably 0.2 to 6, kg per hectare. The amount of spray liquor to be applied is for instance from 10 to 2,000 liters per hectare.

The herbicidal action of the herbicides according to the invention is the same as that of conventional herbicides comprising the same active ingredient at the same active ingredient application rate.

The herbicides of the invention containing from 10 to 65 wt% of active ingredient are prepared by triturating the suspended active ingredient in mills (e.g., sand or Perl mills) with the addition of surfactants and, if desired, protective colloids and antifreezes. The purpose of the latter is to lower to a sufficient degree the freezing point of the water in the herbicide when it is stored in regions where low temperatures prevail.

Examples of protective colloids are cellulosic derivatives, polyvinyl pyrrolidones and polyvinyl alcohols. Examples of antifreezes are ethylene glycol, glycerol and urea.

The amount of protective colloids in the suspensions of the invention is for example from 0 to 10, preferably 4 to 5,% by weight. The amount of antifreeze is for instance from 0 to 10, preferably 5 to 9, % by weight.

Application may be effected for instance in the form of suspensions or dispersions, by spraying, atomizing or watering. The forms of application depend entirely on the purpose for which the agents are being used; in any case they should ensure a fine distribution of the active ingredient.

There may be added to the herbicides (if desired, immediately before use (tank-mix) oils of various types, fungicides, nematocides, insecticides, bactericides, trace elements, fertilizers, antifoams (e.g., silicones), growth regulators, antidotes and other herbicidally effective compounds such as substituted anilines, substituted aryloxycarboxylic acids and salts, esters and amides thereof, substituted ethers, substituted arsonic acids and their salts, esters and amides, substituted benzimidazoles, substituted benzisothiazoles, substituted benzothiadiazinone dioxides, substituted benzoxazines, substituted benzoxazinones, substituted benzothiadiazoles, substituted biurets, substituted quinolines, substituted carbamates, substituted aliphatic carboxylic acids and their salts, esters, and amides, substituted aromatic carboxylic acids and their salts, esters, and amides, substituted carbamoylalkylthiol- or -dithiophosphates, substituted quinazolines, substituted cycloalkylcarbonamidothiazoles, substituted dicarboxylic acids and their salts, esters and, amides, substituted dihydrobenzofuranyl sulfonates, substituted disulfides, substituted dipyridylium salts, substituted dithiocarbamates, substituted dithiophosphroic acids and their salts, esters, and amides, substituted ureas, substituted hexahydro-1H-carbothioates, substituted hydantoins, substituted hydrazides, substituted hydrozonium salts, substituted isoxazole pyrimidones, substituted imidazoles, substituted isothiazole pyrimidones, substituted ketones, substituted naphthoquinones, substituted aliphatic nitriles, substituted aromatic nitriles, substituted oxadiazoles, substituted oxadiazinones, substituted oxadiazolidine diones, substituted oxadiazine diones, substituted phenols and their salts and esters, substituted phosphonic acids and their salts, esters and, amides, substituted phosphonium chlorides, substituted phosphonalkyl glycines, substituted phosphites, substituted phosphoric acids and their salts, esters and, amides, substituted piperidines, substituted pyrazoles, substituted pyrazole alkylcarboxylic acids and their salts, esters and amides, substituted pyrazolium salts, substituted pyrazolium alkyl sulfates, substituted pyridazines, substituted pyridazones, substituted pyridine carboxylic acids and their salts, esters, and amides, substituted pyridines, substituted pyridine carboxylates, substituted pyridinones, substituted pyrimidines, substituted pyrimidones, substituted pyrrolidine carboxylic acid and its salts, esters, and amides, substituted pyrrolidines, substituted pyrrolidones, substituted arylsulfonic acids and their salts, esters and, amides, substituted styrene, substituted tetrahydrooxadiazine diones, substituted tetrahydroxadiazole diones, substituted tetrahydromethanoindenes, substituted tetrahydroxadiazole thiones, substituted tetrahydrothiadiazine thiones, substituted tetrahydrothiadiazole diones, substituted aromatic thiocarbonylamides, substituted thiocarboxylic acids and their salts, esters and, amides, substituted thiol carbamates, substituted thioureas, substituted thiophosphoric acids and their salts, esters and, amides, substituted triazines, substituted triazoles, substituted uracils, and, substituted uretidine diones.

The last-mentioned herbicidal compounds may also be applied before or after the herbicides according to the invention.

The agents may be added to the herbicides according to the invention in a ratio by weight of from 1:10 to 10:1. The same applies to oils, fungicides, nematocides, insecticides, bactericides, antidotes and growth regulators.

The herbicides according to the invention may be employed in cereal crops such as
Avena spp.; Sorghum
Triticum spp.; Zea mays
Hordeum spp.; Panicum miliaceum
Secale spp.; Oryza spp.
Saccharum offinicarum
and in dicotyledon crops such as Cruciferae, e.g.
Brassica spp.; Raphanus spp.
Sinapis spp.; Lepidium spp.
Compositae, e.g.
Lactuca spp.; Carthamus spp.
Helianthus spp.; Scorzonera spp.
Malvaceae, e.g.
Gossypium hirsutum
Leguminosae, e.g.
Medicago spp.; Phaseolus spp.
Trifolium spp.; Arachis spp.
Pisum spp.; Glycine max.
Chenopodiaceae, e.g.
Beta spp.
Spinacia spp.
Solanaceae, e.g.
Solanum spp.; Capsicum annuum
Nicotiania spp.;
Linaceae, e.g.
Linum spp.
Umbelliferae, e.g.
Petroselinum spp.; Apium graveolens
Daucus carota
Rosaceae, e.g. Fragaria
Cucurbitaceae, e.g.
Cucumis spp.; Cucurbita spp.
Liliaceae, e.g.
Allium spp.
Vitaceae, e.g.
Vitis vinifera
Bromeliaceae, e.g.
Ananas sativus The herbicides according to the invention are used for controlling the growth of unwanted plants.

By weeds and unwanted plants are meant all monocotyledonous and dicotyledonous plants which grow in loci where they are not desired.

The agents according to the invention may therefore be used for controlling for instance Gramineae, such as
Cynodon spp.; Dactylis spp.
Digitaria spp.; Avena spp.
Echinochloa spp.; Bromus spp.
Setaria spp.; Uniola spp.
Panicum spp.; Poa spp.
Alopecurus spp.; Leptochloa spp.
Lolium spp.; Brachiaria spp.
Sorghum spp.; Eleusine spp.
Agropyron spp.; Cenchrus spp.
Phalaris spp.; Eragrostis spp.
Apera spp.; Phragmites communis
etc.;
Cyperaceae, such as
Carex spp.; Eleocharis spp.
Cyperus spp.; Scirpus spp.
etc;
dicotyledonous weeds, such as Malvaceae, e.g.
Abutilon theoprasti Hibiscus spp.
Sida spp. Malva spp.
etc;
Compositae, such as
Ambrosia spp.; Centaurea spp.
Lactuca spp.; Tussilago spp.
Senecio spp.; Lapsana communis
Sonchus spp.; Tagetes spp.
Xanthium spp.; Erigeron spp.
Iva spp; Anthemis spp.
Galinsoga spp.; Matricaria spp.
Taraxacum spp.; Artemisia spp.
Chrysanthemum spp.; Bidens spp.
Cirsium spp.; etc.;
Convolvulaceae, such as
Convolvulus spp.; Cuscuta spp.
Ipomoea spp.; Jaquemontia tamnifolia
etc.;
Cruciferae, such as
Barbarea vulgaris; Arabidopsis thaliana
Brassica spp.; Descurainia spp.
Capsella spp.; Draba spp.
Sisymbrium spp.; Coronopus didymus
Thlaspi spp.; Lepidium spp.
Sinapis arvensis; Raphanus spp.
etc.;
Geraniaceae, such as
Erodium spp.; Geranium spp.
etc.;

Primulaceae, such as
Anagallis arvensis; Lysimachia spp.
etc.;
Rubiaceae, such as
Richardia spp.; Diodia spp.
Galium spp.; etc.;
Scrophulariaceae, such as
Linaria spp.; Digitalis spp.
Veronica spp.; etc.;
Solanaceae, such as
Physalis spp.; Nicandra spp.
Solanum spp.; Datura spp.
etc.;
Urticaceae, such as
Urtica spp.
Violaceae, such as
Viola spp.; etc.;
Zygophyllaceae, such as
Tribulus terrestris; etc.;
Euphorbiaceae, such as
Mercurialis annua; Euphorbia spp.
Umbelliferae, such as
Daucus carota; Ammi majus
Aethusa cynapium; etc.;
Commelinaceae, such as
Commelina spp.; etc.;
Labiatae, such as
Lamium spp.; Galeopsis spp.
etc.;
Leguminosae, such as
Medicago spp.; Sesbania exaltata
Trifolium spp.; Cassia spp.
Vicia spp.; Lathyrus spp.
etc.;
Plantaginaceae, such as
Plantago spp.; etc.;
Polygonaceae, such as
Polygonum spp.; Fagopyrum spp.
Rumex spp.; etc.;
Aizoceae, such as
Mollugo verticillata; etc;
Amaranthaceae, such as
Amaranthus spp. etc.;
Boraginaceae, such as
Amsinckia spp.; Anchusa spp.
Myostis spp; Lithospermum spp.
etc.;
Caryophyllaceae, such as
Stellaria spp.; Silene spp.
Spergula spp.; Cerastium spp.
Saponaria spp.; Agrostemma githago
Scleranthus annuus; etc.;
Chenopodiaceae, such as
Chenopodium spp.; Atriplex spp.
Kochia spp.; Monolepsis nuttalliana
Salsola Kali; etc.;
Lythraceae, such as
Cuphea spp.; etc.;
Oxalidaceae, such as
Oxalis spp.
Ranunculaceae, such as
Ranunculus spp.; Adonis spp.
Delphinium spp.; etc.;
Papaveraceae, such as
Papaver spp.; Fumaria offinicalis
etc.;
Onagraceae, such as
Jussiacea spp.; etc.;
Rosaceae, such as
Alchemillia spp.; Potentialla spp.
etc.;
Potamogetonaceae, such as
Potamogeton spp.; etc.;
Najadaceae, such as
Najas spp.; etc.;
Equisetaceae
Equisetum spp.; etc.;
Marsileaceae, such as
Marsilea quadrifolia; etc.;
Polypodiaceae,
Pteridium quilinum
Alismataceae, such as
Alisma spp.; Sagittaria sagittifolia etc.

It is known that an extremely fine product, i.e., small paticle size (up to 100%, depending on duration of grinding, less than 2 $\mu$), may be obtained by milling active ingredient suspensions in, for instance, Perl mills.

The following examples demonstrate the advantageous properties of the herbicides of the invention.

EXAMPLE 1

| Composition of the suspension | wt% |
|---|---|
| 1-phenyl-4-amino-5-chloropyridazone-(6) | 53 |
| dispersant (condensation product of sulfonated phenol, urea and formaldehyde, which has been condensed with a separately prepared phenol-formaldehyde condensate) | 5 |
| ethylene glycol | 10 |
| triisobutyl phosphate | 0.1 |
| water | 31.9 |

Water, ethylene glycol and dispersant are placed in a vessel, and the active ingredient is introduced with stirring. The pH of the suspension is about 8.0 to 9.0.

To homogenize the suspension it is ground in a corundum disc mill. After the triisobutyl phosphate has been added the mixture is ground in a wet-type mill, e.g., stirred ball mill, ball mill or, preferably, a sand mill, with a grinding medium having a diameter of from 0.5 to 1.0 mm until examination of the degree of dispersion in accordance with the filter test (cf. A. Schlottmann, Textil-Praxis, Jan. 1957, p.63) reveals the absence of residue, and the centrifuge test (cf. Richter and Vescia, Melliand-Textilberichte, 6/1965, p. 622) gives values of about 20, 15, 25, 40 or better.

The suspension which is obtained flows well, to all intents and purposes does not settle out, in stable on storage, and disperses very easily in water upon stirring.

EXAMPLE 2

| Composition of the suspension | wt% |
|---|---|
| 1-phenyl-4-amino-5-chloropyridazone-(6) technical grade | 53 |
| dispersant (as in Example 1) | 5 |
| ethylene glycol | 10 |
| triisobutyl phosphate | 0.05 |
| tap water | 31.95 |

The suspension is prepared as in Example 1.

Grinding may take place at an active ingredient content of 55%. The remaining liquid may be added to achieve the final concentration when the desired degree of dispersion has been reached.

To improve miscibility with water (spreading and wetting) there may be added to the suspension a spreader-sticker, e.g., 0.2 to 2% of a tallow fatty alcohol, each mole of alcohol being reacted with 5 moles of ethylene oxide and 13 moles of propylene oxide, and the terminal groups being reacted with vinyl butyl ether.

The suspension which is obtained is slightly thixotropic, flows well after slight stirring, does not settle out, is storage-stable, and disperses uniformly and with great facility upon being poured into water.

EXAMPLE 3

| Composition of the suspension | wt.% |
|---|---|
| 1-phenyl-4-amino-5-chloropyridazone-(6) | 45 |
| dispersant (prepared as in Example 1 of German 1,178,081) | 10 |
| ethylene glycol | 5 |
| water | 40 |

The suspension is prepared as in Example 1.

The centrifuge test gives values of 5, 10, 5, 80 which hardly change even after storage at 60°0 C for several days.

Instead of the above dispersant, a dispersant prepared as in Example 1 of German 1,113,457 may be used, with the same results.

The dispersant employed in Examples 1 and 2 was prepared as follows.

Condensation stage A 94 parts of phenol is sulfonated with 110 parts of 96 to 98% sulfuric acid for 2½ hours at 100° C. The mixture is then cooled and diluted with 40 parts of water. 60 parts of technically pure urea is then added and condensation carried out with 190 parts of 30% formaldehyde at 40° to 60° C for about 2 hours until the condensation product obtained dissolves in water to give a clear solution. After the addition of 35 parts of caustic soda solution (50%) there is obtained a titer of 14 to 16 ml of 1N caustic soda solution.

Condensation stage B 47 parts of phenol, 1 part of caustic soda solution (50%) and 50 parts of 30% formaldehyde are reacted for 1 hour at 50° C and for a further 5 hours at 60° C; the methylol compound obtained is diluted with 12 parts of water, the pH is adjusted with 1 part of 50% sulfuric acid to 3.5, and the mixture is allowed to stand for from 0 to 4 hours.

The stage 2 product is then run into the stage 1 product and the mixture is stirred for 1 hour at 40° C. Subsequently, the mixture is neutralized to a pH of from 8.0 to 8.5 with 75 parts of caustic soda solution (50%).

We claim:
1. A herbicide composition comprising a stable, aqueous suspension of 10 to 65% by weight of 1-phenyl-4-amino-5-chloropyridazone-(6) or 1-phenyl-4-amino-5-bromopyridazone-(6), and, as the dispersant, a condensation product of a sulfonated phenol free from condensed ring systems, urea and formaldehyde, and which condensation product has been after-treated with a phenol and formaldehyde.

2. A herbicide composition comprising a stable, aqueous suspension of 10 to 65% by weight of 1-phenyl-4-amino-5-chloropyridazone-(6) or 1-phenyl-4-amino-5-bromopyridazone-(6), and, as the dispersant, a condensation product of a sulfonated phenol free from condensed ring system, urea and formaldehyde, and which condensation product has been after-treated with a phenol and formaldehyde, said condensation product being the condensate of said phenol, urea and formaldehyde in a molar ratio of 1:1 to 1.5:1.7 to 2.2, respectively.

3. A herbicide composition as claimed in claim 2, wherein the 1-phenyl-4-amino-5-chloropyridazone-(6) or 1-phenyl-4-amino-5-bromopyridazone-(6) is in the form of ground particles thereof, at least 80% of which particles are smaller than 2 $\mu$.

4. A herbicide composition as claimed in claim 1, wherein the 1-phenyl-4-amino-5-chloropyridazone-(6) or 1-phenyl-4-amino-5-bromopyridazone-(6) is in the form of ground particles thereof, at least 80% of which particles are smaller than 2 $\mu$.

5. A herbicide composition as claimed in claim 2 wherein said dispersant is the condensation product of sulfonated phenol, urea and formaldehyde in said molar ratio, and said after-treatment of said condensation product is done with methylolated phenol.

6. A herbicide composition as claimed in claim 5, wherein the 1-phenyl-4-amino-5-chloropyridazone-(6) or 1-phenyl-4-amino-5-bromopyridazone-(6) is in the form of ground particles thereof, at least 80% of which particles are smaller than 2 $\mu$.

7. A herbicide composition as claimed in claim 1, wherein the 1-phenyl-4-amino-5-chloropyridazone-(6) or 1-phenyl-4-amino-5-bromopyridazone-(6) is in the form of ground particles thereof, at least 80% of which particles are smaller than 2 $\mu$, said ground particles being obtained by grinding said 1-phenyl-4-amino-5-chloropyridazone-(6) or 1-phenyl-4-amino-5-bromopyridazone-(6) in an aqueous medium containing said dispersant.

* * * * *